(12) United States Patent
Kawaguchi et al.

(10) Patent No.: US 9,193,649 B2
(45) Date of Patent: Nov. 24, 2015

(54) PURIFYING METHOD AND MANUFACTURING METHOD OF 2,3,3,3-TETRAFLUOROPROPENE

(71) Applicant: ASAHI GLASS COMPANY, LIMITED, Chiyoda-ku (JP)

(72) Inventors: Satoshi Kawaguchi, Tokyo (JP); Hirokazu Takagi, Tokyo (JP); Masaaki Tsuzaki, Tokyo (JP); Masato Fukushima, Tokyo (JP); Hidekazu Okamoto, Tokyo (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 0 days.

(21) Appl. No.: 14/305,476

(22) Filed: Jun. 16, 2014

(65) Prior Publication Data
US 2014/0305161 A1    Oct. 16, 2014

Related U.S. Application Data

(63) Continuation of application No. PCT/JP2012/083449, filed on Dec. 25, 2012.

(30) Foreign Application Priority Data

Dec. 28, 2011   (JP) .................................. 2011-289691

(51) Int. Cl.
*C07C 17/383*   (2006.01)
*C07C 21/18*    (2006.01)
(Continued)

(52) U.S. Cl.
CPC ............... *C07C 17/383* (2013.01); *C07C 17/25* (2013.01); *C07C 17/354* (2013.01)

(58) Field of Classification Search
CPC .................................................. C07C 17/383
See application file for complete search history.

(56) References Cited

U.S. PATENT DOCUMENTS 7,982,073 B2 *  7/2011  Nappa et al. ................. 570/156
8,399,722 B2    3/2013  Kawaguchi et al.
(Continued)

FOREIGN PATENT DOCUMENTS

| CA | 2 627 898 | 5/2007 |
| CN | 101351428 | 1/2009 |

(Continued)

OTHER PUBLICATIONS

International Search Report issued Feb. 5, 2013 in PCT/JP2012/083449 filed Dec. 25, 2012.
(Continued)

*Primary Examiner* — Fereydoun G Sajjadi
*Assistant Examiner* — Medhanit Bahta
(74) *Attorney, Agent, or Firm* — Oblon, McClelland, Maier & Neustadt, L.L.P.

(57) ABSTRACT

There is provided a method and an apparatus for efficiently obtaining 2,3,3,3-tetrafluoropropene with low contents of both organic impurities and water. The method for continuously purifying crude 2,3,3,3-tetrafluoropropene containing water and one or more organic impurities, the method including using an apparatus having a distillation column with X stages ($3 \leq X$, the stage closest to a column top is the first stage) and a unit for cooling and condensing a distillate; supplying the crude 2,3,3,3-tetrafluoropropene to an m-th stage ($n+1 \leq m \leq X$, $2 \leq n \leq X-1$) of the distillation column, recirculating at least part of the distillate cooled and condensed in the unit for cooling and condensing to an h-th stage ($1 \leq h \leq n-1$) of the distillation column; and taking out a liquid phase part of an n-th stage of the distillation column to obtain a purified product of 2,3,3,3-tetrafluoropropene.

12 Claims, 7 Drawing Sheets

(51) Int. Cl.
*C07C 17/25* (2006.01)
*C07C 17/354* (2006.01)

(56) References Cited

U.S. PATENT DOCUMENTS

| | | | |
|---|---|---|---|
| 8,530,710 | B2 | 9/2013 | Takagi et al. |
| 8,530,711 | B2 | 9/2013 | Kawaguchi et al. |
| 8,642,820 | B2 | 2/2014 | Seki et al. |
| 8,766,021 | B2 | 7/2014 | Kawaguchi et al. |
| 2007/0100175 | A1 | 5/2007 | Miller et al. |
| 2011/0160500 | A1 | 6/2011 | Takahashi |
| 2012/0261252 | A1* | 10/2012 | Knapp ............................. 203/62 |

FOREIGN PATENT DOCUMENTS

| | | |
|---|---|---|
| CN | 102131754 | 6/2011 |
| GB | 2492847 A * | 1/2013 |
| JP | 8-12612 | 1/1996 |
| JP | 2009-613719 | 4/2009 |
| JP | 2012/500185 | 1/2012 |
| KR | 10-2008-0066837 | 7/2008 |
| WO | 2007/053736 | 5/2007 |
| WO | 2010/024366 | 3/2010 |

OTHER PUBLICATIONS

International Preliminary Report on Patentability and Written Opinion issued Jul. 10, 2014 in PCT/JP2012/083449 (submitting English translation only).

Supplementary European Search Report dated Jun. 29, 2015 issued in corresponding European patent application No. 12861259.5.

* cited by examiner

PURIFYING METHOD AND MANUFACTURING METHOD OF 2,3,3,3-TETRAFLUOROPROPENE

CROSS-REFERENCE TO RELATED APPLICATIONS

This application is a continuation of prior International Application No. PCT/JP2012/083449, filed on Dec. 25, 2012 which is based upon and claims the benefit of priority from Japanese Patent Application No. 2011-289691 filed on Dec. 28, 2011, the entire contents of all of which are incorporated herein by reference.

FIELD

The present invention relates to a purifying method and a purifying apparatus of 2,3,3,3-tetrafluoropropene and a manufacturing method of 2,3,3,3-tetrafluoropropene having the purifying method.

BACKGROUND

Conventionally, as a refrigerant for automobile air conditioners or the like, 1,1,1,2-tetrafluoroethane (HFC-134a) has been widely used. However, HFC-134a has a high global warming potential (GWP) of 1430, and hence its use has become restricted due to movement toward restricting refrigerant having high GWP in recent years, for example, prohibiting use of a refrigerant with GWP of 150 or more in new models of automobiles in EU from the year 2011, and the like. Here, in this description, for halogenated hydrocarbons, an abbreviation of a chemical compound will be described in parentheses after a chemical compound name, but in this description such an abbreviation is also used instead of a chemical compound name as necessary.

Then, as an alternative refrigerant for HFC-134a, use of 2,3,3,3-tetrafluoropropene (HFO-1234yf) with a quite low GWP of 4 is becoming popular. In manufacturing HFO-1234yf, alkaline washing and water washing are performed for removing acids used or generated such as hydrofluoric acid, hydrochloric acid, and the like, and thus crude liquid often contains water besides fluorine-based low-molecular organic impurities of intermediates, by-products, non-reacted raw materials, and the like.

When such crude liquid of HFO-1234yf is purified by distillation, HFO-1234yf and water form an azeotrope mixture, and thus water contained in the crude liquid condenses in a column-top reflux line, and water in an obtained product increases. Thus, Patent Reference 1 (WO2010/024366) describes a manufacturing method of HFO-1234yf which makes an HFO-1234yf product with less water from a bottom product obtained from a bottom part of a distillation column.

However, among the fluorine based low-molecular organic impurities contained in the HFO-134yf crude liquid, there are many organic impurities having higher boiling point than that of HFO-1234yf, and such many organic impurities are mixed into the bottom product obtained from the bottom part of the distillation column. Thus, it has been necessary to further remove the organic impurities in another process.

SUMMARY

The present invention has been made from the above-described viewpoint, and an object there of is to provide a purifying method and a purifying apparatus, and a manufacturing method for efficiently obtaining highly pure 2,3,3,3-tetrafluoropropene with low contents of both organic impurities and water.

The present invention provides a method for continuously purifying crude 2,3,3,3-tetrafluoropropene containing water and an organic impurity, the method including: using an apparatus having a distillation column with X stages (where "X" is an integer of 3 or larger, and the stage closest to a column top is the first stage) and a unit for cooling and condensing a distillate taken out from a column top of the distillation column; supplying the crude 2,3,3,3-tetrafluoropropene to an m-th stage (where "m" is an integer satisfying $n+1 \leq m \leq X$ and "n" is an integer satisfying $2 \leq n \leq X-1$) of the distillation column; recirculating at least part of the distillate cooled and condensed in the unit for cooling and condensing to an h-th stage (where "h" is an integer satisfying $1 \leq h \leq n-1$) of the distillation column; and taking out a liquid phase part of an n-th stage of the distillation column to obtain a purified product of 2,3,3,3-tetrafluoropropene.

The present invention provides an apparatus for continuously purifying crude 2,3,3,3-tetrafluoropropene containing water and an organic impurity, the apparatus including a distillation column with X stages (where "X" is an integer of 3 or larger, and the stage closest to a column top is the first stage) and a unit for cooling and condensing a distillate taken out from a column top of the distillation column, wherein the unit for cooling and condensing has a recirculation liquid discharge port discharging at least part of the cooled and condensed distillate as a recirculation liquid, and the distillation column has a supply port supplying the crude 2,3,3,3-tetrafluoropropene to an m-th stage (where "m" is an integer satisfying $n+1 \leq m \leq X$ and "n" is an integer satisfying $2 \leq n \leq X-1$), a supply port recirculating the recirculation liquid to an h-th stage (where "h" is an integer satisfying $1 \leq h \leq n-1$); and a discharge port through which a liquid phase part of an n-th stage is taken out as a purified product of 2,3,3,3-tetrafluoropropene.

The present invention provides a manufacturing method of 2,3,3,3-tetrafluoropropene, the method including the above-described purifying method of 2,3,3,3-tetrafluoropropene of the present invention.

According to the present invention, highly pure 2,3,3,3-tetrafluoropropene with low contents of both organic impurities and water can be obtained efficiently.

DETAILED DESCRIPTION

Figure 1:
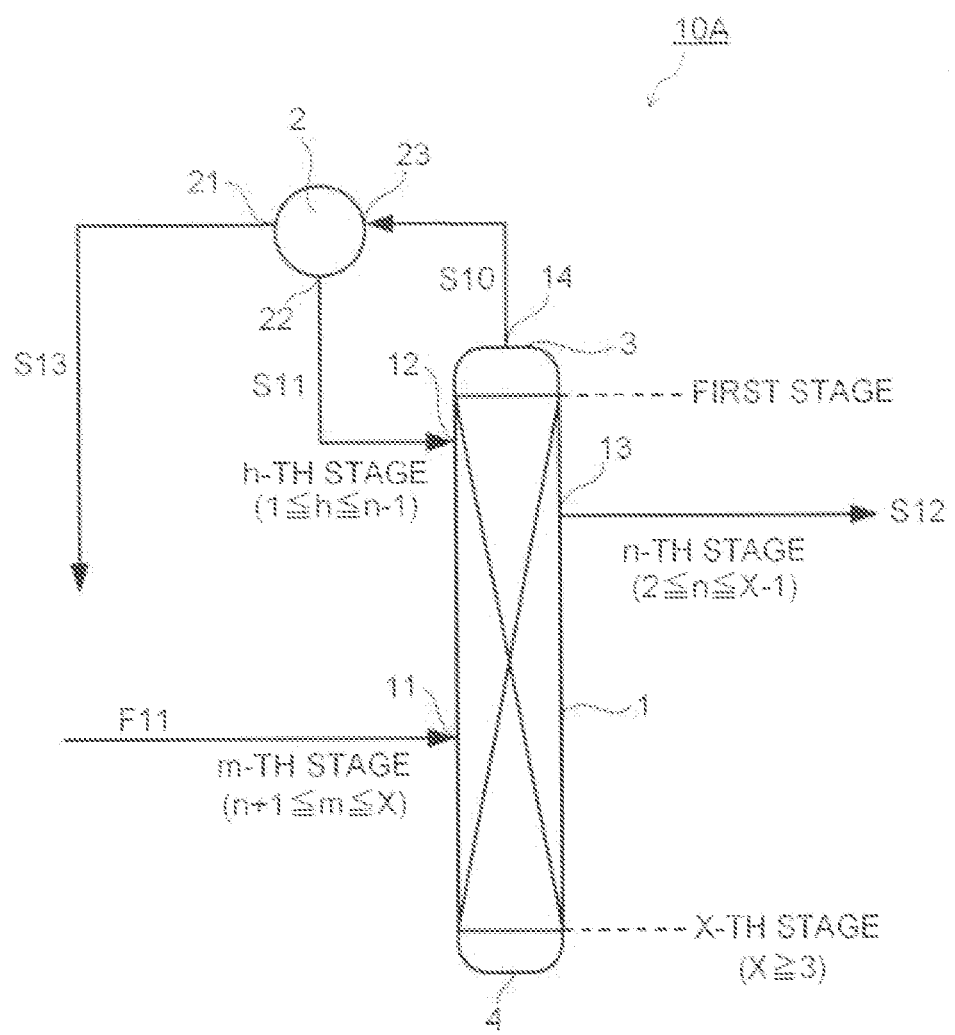
FIG. 1 is a schematic diagram illustrating an example of an embodiment of a purifying apparatus of HFO-1234yf of the present invention.

Hereinafter, embodiments of the present invention will be described. Note that the present invention should not be construed as being limited to the following description. The embodiment of the present invention provides a method for continuously purifying crude 2,3,3,3-tetrafluoropropene containing water and one or more organic impurities, the method including: using an apparatus having a distillation column with X stages (where "X" is an integer of 3 or larger, and the stage closest to a column top is the first stage) and a unit for cooling and condensing a distillate taken out from a column top of the distillation column; supplying the crude 2,3,3,3-tetrafluoropropene to an m-th stage (where "m" is an integer satisfying n+1≤m≤X and "n" is an integer satisfying 2≤n≤X−1) of the distillation column; recirculating at least part of the distillate cooled and condensed in the unit for cooling and condensing to an h-th stage (where "h" is an integer satisfying 1≤h≤n−1) of the distillation column; and taking out a liquid phase part of an n-th stage of the distillation column to obtain a purified product of 2,3,3,3-tetrafluoropropene.

Crude HFO-1234yf

The crude HFO-1234yf which is the target of the purifying method of the embodiment according to the present invention contains water and one or more organic impurities. The organic impurities contained in the crude HFO-1234yf include non-reacted products of raw materials used when manufacturing the HFO-1234yf by a conventional publicly known manufacturing method as well as intermediates and by-products generated in a manufacturing process, and the like.

For example, when HFO-1234yf is manufactured using an isomer mixture of dichloropentafluoropropane ($C_3HCl_2F_5$ (HCFC-225)), the crude HFO-1234yf contains organic impurities as follows.

In a manufacturing method of HFO-1234yf by using the isomer mixture of HCFC-225 as a raw material, as described in reaction route (1) below, 1,1-dichloro-2,2,3,3,3-pentafluoropropane ($CHCl_2CF_2CF_3$, HCFC-225ca) in the raw material is selectively dehydrofluorinated to manufacture 1,1-dichloro-2,3,3,3-tetrafluoropropene ($CF_3CF=CCl_2$, CFO-1214ya), and the obtained CFO-1214ya is reduced to manufacture HFO-1234yf.

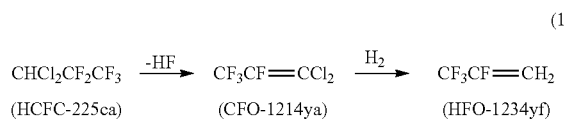

(1)

In the manufacturing method using the HCFC-225 isomer mixture as a raw material, the organic impurities include following chemical compounds. The chemical compounds contained in the raw material include HCFC-225ca (boiling point: 51° C.) and its isomers, 1,3-dichloro-1,2,2,3,3-pentafluoropropane ($CHClFCF_2CClF_2$, HCFC-225cb, boiling point: 56.1° C.), 2,2-dichloro-1,1,3,3,3-pentafluoropropane ($CHF_2CCl_2CF_3$, HCFC-225aa, boiling point: 52° C.), and the like.

Further, the intermediate products include CFO-1214ya (boiling point: 46.4° C.), 1-chloro-2,3,3,3-tetrafluoropropene ($CF_3CF=CHCl$, HCFO-1224yd, boiling point: 15° C.) of an intermediate product in a reaction system generating HFO-1234yf from CFO-1214ya, and the like.

Moreover, the by-products include 1,1,1,2-hexafluoropropane ($CF_3CHFCH_3$, HFC-254eb, boiling point: −6° C.) which is a reductant of HCFC-225ca, 1,1,3,3,3-pentafluoropropene ($CF_3CH=CF_2$, HFO-1225zc, boiling point: −20.7° C.) which is obtained by reduction after HCFC-225aa has undergone a dehydrochlorination reaction, 3,3,3-trifluoropropene ($CF_3CH=CH_2$, HFO-1234zf, boiling point: −22° C.) and 3,3-difluoropropene ($CHF_2CH=CH_2$, HFO-1252zf, boiling point: −26.5° C.) which are over-reduced products of HFO-1234yf and the like.

HFO-1234yf has a boiling point at −29° C. by the purifying method of the embodiment according to the present invention, even in the case of organic impurities whose boiling point are close to that of HFO-1234yf, or specifically, when organic impurities contain organic compounds whose boiling point are from −40 C. to −10° C., they can be separated effectively. When the isomer mixture of HCFC-225 is used as a raw material to manufacture HFO-1234yf via the reaction route, the organic compounds whose boiling point are from −40° C. to −10° C. includes HFO-1225zc, HFO-1234yf, HFO-1252zf, and the like.

Further, as organic compounds whose boiling point are −40° C. to −10° C. among organic impurities contained in the crude HFO-1234yf obtained via a reaction route other than using the isomer mixture of HCFC-225 as a raw material to manufacture HFO-1234yf, besides HFO-1225zc, HFO-1243zf and HFO-1252zf, for example, there are 1,2,3,3,3-pentafluoropropene ($CF_3CF=CHF$, HFO-1225ye, boiling point: −18° C.), 1,3,3,3-tetrafluoropropene ($CF_3CH=CHF$, HFO-1234ze, boiling point: −16° C.), 1,1,2,3,3,3-hexafluoropropene ($CF_3CF=CF_2$, PFO-1216yc, boiling point: −29° C.), 1,1,1,2,2-pentafluoropropane ($CF_3CF_2CH_3$, HFC-245cb, boiling point: −18.3° C.), and the like.

Among them, PFO-1216yc, HFO-1225ye, HFO-1234ze, and the like are organic compounds whose boiling point are −40° C. to −10° C. which can become organic impurities when HFO-1234yf is manufactured via, for example, the following reaction route (2) using PFO-1216yc as a raw material chemical compound.

[Chemical Formula 2]

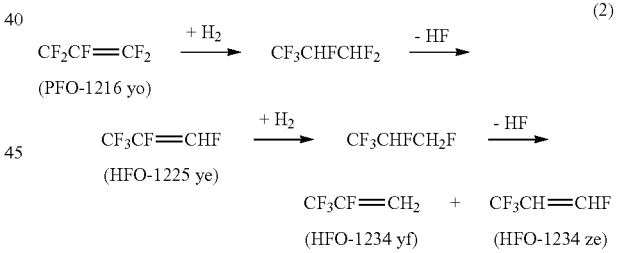

(2)

Further, HFC-245cb is an organic compound whose boiling point is −40° C. to −10° C. which can become the organic impurity when HFO-1234yf is manufactured via, for example, the following reaction route (3) using 1,2,3-trichloropropane as a raw material chemical compound.

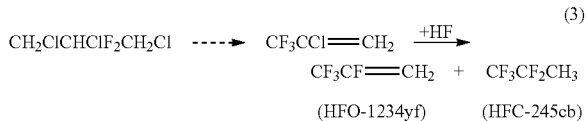

(3)

Here, the crude HFO-1234yf obtained by manufacturing of HFO-1234yf via the reaction route (2) or the reaction route (3) normally contains, similarly to those described in the reaction route (1), organic compounds whose boiling point are out of the range of −40° C. to −10° C. among non-reacted products of raw materials and intermediates, by-products, and the like generated in the manufacturing process, other than the organic compounds whose boiling point are −40° C. to −10° C.

Note that in Patent Reference 1, HFC-245cb is an organic compound used as a raw material chemical compound for manufacturing HFO-1234yf together with 1,1,1,2,3-pentafluoropropane ($CF_3CHFCH_2F$, HFC-245eb, boiling point −1° C.). In Patent Reference 1, HFC-245cb and HFC-245eb are dehydrofluorinated to manufacture HFO-1234yf, and for removal of organic impurities such as non-reacted raw materials, there is employed a method performing the removal by using a distillation column different from the distillation column for water removal.

The organic compounds contained as impurities in the crude HFO-1234yf are as described above. Further, since acid such as hydrogen fluoride hydrogen chloride, and the like are used or generated in all of the manufacturing methods exemplified above, the water contained as impurities in the crude HFO-134yf is water that is brought in by alkaline washing or water washing performed for removing such acid.

In the purifying method of HFO-1234yf of the embodiment according to the present invention, the contents of organic impurities and water in the crude HFO-1234yf containing water and organic impurities in this manner are decreased efficiently with one distillation column by the above-described constitution, so as to produce a highly pure HFO-1234yf purified product. Specifically, by the purifying method of HFO-1234yf of the embodiment according to the present invention, crude HFO-1234yf in which content of HFO-1234yf relative to the total amount of the organic compounds in the crude HFO-1234yf is 5 mass % or more and less than 99.5 mass % can be made as a HFO-1234yf purified product in which content of HFO-1234yf relative to the total amount of the organic compounds in the purified product is 99.5 mass % or more, furthermore preferably 99.8 mass % or more.

Note that when organic impurities whose boiling point are particularly close to that of HFO-1234yf, or is specifically in the range of −40° C. to −10° C. are contained in the crude HFO-1234yf by ratio of 10 mass % or more to the amount of HFO-1234yf in the crude HFO-1234yf, it is necessary to have measures such as increasing the number of stages X of the distillation columns, which will be described below, in order to obtain the HFO-1234yf purified product in which content of HFO-1234yf relative to the total amount of the organic compounds in the purified product is 99.5 mass % or more. Accordingly, regarding the organic impurities whose boiling point are in the range of −40° C. to −10° C., the reaction conditions are preferably controlled by a conventional publicly known method so that the content of them relative to the amount of HFO-1234yf in the obtained crude HFO-1234yf does not become 10 mass % or more in the above-described various reaction stages.

Further, by the purifying method of HFO-1234yf of the embodiment according to the present invention, for example, crude HFO-1234yf in which content of water relative to HFO-1234yf is 100 ppm or less, preferably 50 ppm or less, can be made as an HFO-1234yf purified product in which content of water relative to HFO-1234yf is 20 ppm or less. Further, by the purifying method of HFO-1234yf of the embodiment according to the present invention, for example, crude HFO-1234yf in which content of water relative to HFO-1234yf is more than 20 ppm can be made as an HFO-1234yf purified product in which content of water relative to HFO-1234yf is 20 ppm or less, preferably 10 ppm or less.

Purifying Method

In the purifying method of the embodiment according to the present invention, the crude HFO-1234yf as described above is purified by the following method by using an apparatus having a distillation column with X stages (where "X" is an integer of 3 or larger, and the stage closest to a column top is the first stages and a unit for cooling and condensing a distillate taken out from a column top of the distillation column.

The crude HFO-1234yf is supplied to an m-th stage (where "m" is an integer satisfying $n+1 \leq m \leq X$ and "n" is an integer satisfying $2 \leq n \leq X-1$) of the distillation column, at least part of the distillate cooled and condensed in the unit for cooling and condensing is recirculated to an h-th stage (where "h" is an integer satisfying $1 \leq h \leq n-1$) of the distillation column, and a liquid phase part of the n-th stage of the distillation column is taken out to obtain it as a purified product of HFO-1234yf.

In the purifying method of the embodiment according to the present invention, at least part of the distillate cooled and condensed in the unit for cooling and condensing is recirculated as recirculation liquid to the h-th stage of the distillation column. The distillate to be recirculated as recirculation liquid to the distillation column may be part or all of the distillate taken out from the column top. For example, when the distillate recirculated as recirculation liquid to the distillation column is part of the distillate taken out from the column top, the part of the distillate may be taken out from the unit for cooling and condensing, and the remainder may be taken as the recirculation liquid. The distillate taken out from the column top has a composition with a high water content due to the azeotropic nature of HFO-1234yf and water, and thus when all of it is taken as the recirculation liquid and recirculated to the distillation column, the water content tends to increase through the entire distillation column while it is operated for a long time. Therefore, taking out the part of the distillate can suppress the water content in the distillation column to a certain amount or less, which is preferable.

In the purifying method of HFO-1234yf of the embodiment according to the present invention, moreover, it is preferred to add operations to subject the part of the distillate taken out from the unit for cooling and condensing to a dehydration treatment, and supply an obtained first treated product to the k-th stage (where "k" is an integer satisfying $n+1 \leq k \leq m$) of the distillation column. Thus, water which easily concentrates in the distillation column can be efficiently discharged to the outside of the distillation column, and useful components mainly constituted of HFO-1234yf can be returned to the distillation column. In this case, preferably, the k-th stage supplying the first treated product to the distillation column is the same stage as the m-th stage supplying the crude HFO-1234yf to the distillation column, that is, k=m. Further, as a method for discharging water which easily concentrates in the distillation column to the outside of the distillation column, a method subjecting the recirculation liquid to the dehydration treatment before recirculating it to the distillation column and then recirculating it to the distillation column may also be used.

The purifying method of the embodiment according to the present invention can be, for example, carried out by using an example of an embodiment of a purifying apparatus of HFO-1234yf of the present invention, specifically, an example of an embodiment of a purifying apparatus of the present invention for which a schematic diagram is illustrated in FIG. 1.

A purifying apparatus 10 of the embodiment illustrated in FIG. 1 is an apparatus having a distillation column 1 with X stages (where "X" is an integer of 3 or larger, and the stage closest to a column top is the first stage) and a unit 2 for cooling and condensing a distillate S10 after taking out the distillate S10 from a column top 3 of the distillation column 1.

The distillation column 1 has a supply port 11 for supplying crude HFO-1234yf (F11) to the m-th stage (where "m" is an integer satisfying n+1≤m≤X and "n" is an integer satisfying 2≤n≤X−1), a supply port 12 (hereinafter also referred to as a "recirculation liquid supply port 12") recirculating recirculation liquid sent from the unit 2 for cooling and condensing to the h-th stage (where "h" is an integer satisfying 1≤h≤n−1), and a discharge port 13 (hereinafter also referred to as a "purified product discharge port 13") through which a liquid phase part of the n-th stage is taken out as a purified product S12 of HFO-1234yf.

The unit 2 for cooling and condensing has a distillate supply port 23 through which the distillate S10 taken out from a column top 3 of the distillation column 1 is supplied, a discharge port 21 (hereinafter also referred to as a "distillate discharge port 21") provided to be capable of opening and closing to allow taking out part S13 of the distillate S10, and a recirculation liquid discharge port 22 through which a remainder S11 is taken out as recirculation liquid. Further, the distillate discharge port 21 has a device capable of adjusting the amount of taking out the part S13 of the distillate S10. Note that in the unit 2 for cooling and condensing, when the distillate discharge port 21 is closed, all of the distillate S10 can be taken out as the recirculation liquid S11 through the recirculation liquid discharge port 22 and recirculated to the distillation column 1. In a state that the distillate discharge port 21 is open, the part S13 of the distillate S10 is taken out and the remainder is taken out as S11 (recirculation liquid) through the recirculation liquid discharge port 22.

Hereinafter, the purifying method of the embodiment according to the present invention will be described with reference to the example of the embodiment of the purifying apparatus of the present invention for which a schematic diagram is illustrated in FIG. 1.

The number X of stages of the distillation column 1 only need to be three or more.

Although it depends on the purity of the supplied crude HFO-1234yf, X is preferably 10 or more, particularly preferably 20 or more in order to increase the purity of the purified product. Although there is no particular upper limit for X, the upper limit is preferably about 50, more preferably about 40, in consideration of operability, installation workability, and the like. Regarding the positions of respective stages of the distillation column 1, the closest stage to the column top 3 is the first stage, and the closest stage to a column bottom 4 is the X-th stage. Further, when the positional relation of stages is mentioned, the stage on the column top 3 side of a certain stage will be referred to as an upper stage, and the stage on the column bottom 4 side will be referred to as a lower stage.

Although the size of the distillation column 1 depends on the purity and the amount of treating the crude HFO-1234yf, an inside diameter thereof can be about 100 mm to 2000 mm. A height thereof depends on an inside diameter or the number X which the distillation column 12 has. For example, when the inside diameter is 300 mm to 1000 mm, the height of one stage can be designed to be 0.5 mm to 1.0 mm. Materials for the distillation column 1 are not particularly limited as long as they do not react with respective components contained in the crude HFO-1234yf.

Further, regarding temperatures of the distillation column 1, temperature Tt in the vicinity of the column top 3 is preferably 10° C. to 50° C., and temperature Tb in the vicinity of the column bottom 4 is preferably 50° C. to 150° C. Tt is more preferably 20° C. to 40° C., and Tb is more preferably 80° C. to 120° C. The temperature Tb in the vicinity of the column bottom 4 can be adjusted by heating the column bottom with steam or the like. Further, the temperature Tt in the vicinity of the column top 3 can be adjusted by the temperature and supply amount of the remainder S11 of the distillate S10 returned to the h-th stage of the distillation column 1 as the recirculation liquid from the unit 2 for cooling and condensing. By setting the temperatures in the distillation column 1 within the above-described ranges, the HFO-1234yf can be purified efficiently. The pressure inside the distillation column 1 is preferably adjusted to, for example, 0.3 MPa to 1.0 MPa, more preferably 0.5 MPa to 0.8 MPa with a pressure regulating valve or the like. By having the pressure in the distillation column 1 within these ranges, HFO-1234yf can be purified efficiently.

The crude HFO-1234yf (F11) is supplied from the supply port 11 disposed in the m-th stage (where "m" is an integer satisfying n+1≤m≤X and "n" is an integer satisfying 2≤n≤X−1) of the distillation column 1. Regarding temperature of the supplied crude HFO-1234yf (F11), preferably, it is adjusted to 20° C. to 80° C., more preferably 40° C. to 60° C. from the viewpoint of preventing disturbance of vapor-liquid equilibrium and decrease in number of stages. The position of the supply port 11 is chosen appropriately from any stages of (n+1)-th stage to X-th stage of the distillation column 1. That is, the supply port 11 is provided on a stage lower than the purified product discharge port 13, which is disposed in the n-th stage for taking out the purified product S12 of HFO-1234yf. In the embodiment according to the present invention, the supply port 11 is preferably provided in a stage lower than (n+2)-th stage. Further, although it depends on the number X of stages of the distillation column 1, for example, when X is 20 to 40, the supply port 11 is preferably disposed in a stage lower than the (n+2)-th stage and higher than the stage of the large number between n+20 and X−10.

In the embodiment according to the present invention, the purified product of HFO-1234yf is taken out as a liquid phase part of the n-th stage (where "n" is an integer satisfying 2≤n≤X−1) from the purified product discharge port 13 for the HFO-134yf purified product S12, which is disposed in the n-th stage of the distillation column 1. The purified product discharge port 13 may be provided in any stage from the second stage to the (X−1)-th stage of the distillation column 1.

In the distillation column 1, the closer it is to the column bottom 4, the higher the concentration of organic impurities with a higher boiling point than HFO-1234yf in the crude HFO-1234yf in the liquid phase part that can be obtained. Since HFO-1234yf and water are azeotropic, the closer it is to the column top 3 of the distillation column 1, the higher the concentrations of both water and HFO-1234yf in the liquid phase part that can be obtained, but the closer it is to the column top 3, the higher the tendency of the content of water relative to HFO-1234yf.

In a conventional purifying method, the distillate obtained from the column top is cooled and condensed and taken as the HFO-1234yf purified product, and thus the purified product obtained here has a high water content, which makes it necessary to further remove water in another step.

In the purifying method of the embodiment according to the present invention, recirculation to the distillation column of the recirculation liquid S11 obtained by cooling and condensing at least part of the distillate S10 in the unit 2 for cooling and condensing is performed, and meanwhile taking out the obtained liquid phase part from any stage chosen from stages of second and thereafter and stages higher by one or more than the lowest stage (X-th stage) of the distillation column 1 and making it as the HFO-1234yf purified product S12, it is made possible to obtain an HFO-1234yf purified product with a low water content relative to HFO-1234yf.

Note that although it depends on the number X of stages of the distillation column 1, when X is 20 to 40 for example, the n-th stage where the purified product discharge port 13 is disposed is preferably the second stage or a stage lower than the second stage and higher than the stage of a small number between 20 and X−10 from the viewpoint of obtaining a product with high purity and low water content. From the same point of view, the second to tenth stages are more preferable.

On the other hand, in the purifying method of the embodiment according to the present invention, the distillate S10 discharged from a discharge port 14 (hereinafter also referred to as a "column top discharge port 14") in the vicinity of the column top 3 of the distillation column 1 is supplied to the unit 2 for cooling and condensing. In the unit 2 for cooling and condensing the distillate S10 is cooled and condensed by, for example, a method of cooling the distillate S10 by a refrigerant at 30° C. or less to change it to a liquid phase, or the like. In the unit 2 for cooling and condensing, when the part S13 of the distillate S10 is taken out through the distillate port 21, the part S13 of the distillate S10 is taken out through the distillate discharge port 21 specifically as a vapor phase or liquid phase before or after it is cooled and condensed. S11 that is the remainder when the part S13 is taken out through the distillate S10, on the whole when it is not, is taken out as a liquid phase through the recirculation liquid discharge port 22 and is recirculated as recirculation liquid to the h-th stage (where "h" is an integer satisfying 1≤h≤n−1 and "n" is an integer satisfying 2≤n≤X−1) of the distillation column 1. Hereinafter, as necessary, the part S13 of the distillate S10 taken out through the distillate discharge port 21 will be referred to as a "taken-out distillate" S13, and the remainder S11 of the distillate S10 will be referred to as a "recirculation distillate" S11.

Note that the unit 2 for cooling and condensing may have, although note illustrated, a device to remove nitrogen gas, which is supplied to the distillation column by accompanying the crude HFO-1234yf from the reaction system or the like, and finally brought into the unit for cooling and condensing, or organic impurities whose boiling point are lower than that of HFO-1234yf, in a vapor phase state when it is cooled and condensed.

The h-th stage that is the position where the recirculation distillate S11 is recirculated as the recirculation liquid to the distillation column 1 is not limited in particular as long as it is the first to the (n−1)-th stage. That is, it is not particularly limited as long as disposed in any stage closer to the column top 3 than the purified product discharge port 13 provided at the n-th stage for taking out the HFO-1234yf purified product from the distillation column 1, but it is preferably the first or second stage from the viewpoint of increasing distillation efficiency.

Here, by taking out part of the distillate S10 taken out from the column top as the taken-out distillate S13 as described above, the water content in the distillation column can be suppressed to a certain amount or less. Thus, the content of water relative to HFO-1234yf in the purified product S12 of HFO-1234yf made by taking out the liquid phase part in the n-th stage of the distillation column 1 can be kept stably and sufficiently low. That is, in the method of the embodiment according to the present invention, preferably, distillation is performed while part of the distillate S10 taken out of the column top is taken out as the taken-out distillate S13 and the remainder is recirculated to the distillation column as the recirculation distillate S11. Note that, preferably, the ratio between the amount of discharge of the taken-out distillate S13 and the supply amount of the crude HFO-1234yf (F11) supplied to the distillation column 1 is specifically adjusted as follows.

For example, in order to make the crude HFO-1234yf (F11) in which content of water relative to HFO-1234yf is 100 ppm or less, preferably 50 ppm or less, or the crude HFO-1234yf (F11) in which content of water relative to HFO-1234yf is more than 20 ppm become the HFO-1234yf purified product S12 in which content of water relative to HFO-1234yf is 20 ppm or less, it is preferred to set Sw13:Fw11 in the range of 0.01:1 to 1:1, furthermore preferably in the range of 0.03:1 to 0.1:1 in the case where the discharge amount (mass/H) of the taken-out distillate S13 to Sw13, and the supply amount (mass/H) of the crude HFO-1234yf (F11) is Fw 11.

Further, in the case where the discharge amount (mass/H) of the distillate S10 in the distillation column 1 is Sw10, the supply amount (mass/H) of the recirculation distillate S11 is Sw11, and the discharge amount of HFO-1234yf purified product S12 is Sw12, Sw13:Sw11 is preferably in the range of 0.01:1 to 1:1, furthermore preferably in the range of 0.03:1 to 0.1:1. Preferably, Sw12:Fw11 is in the range of 0.005:1 to 0.2:1, furthermore preferably in the range of 0.01:1 to 0.1:1.

Note that in the continuous purifying of the crude HFO-1234yf by using the purifying apparatus 10 of the embodiment of the present invention, it normally takes a few hours from the start of operation of the purifying apparatus 10A until a material balance and composition reach an equilibrium state between the supplied products and the discharged products in the distillation column 1 and the unit 2 for cooling and condensing. The purity of HFO-1234yf in all the organic compounds in the above-described obtained purified product S12 of HFO-1234yf and the content of water relative to HFO-1234yf are those when this equilibrium state is reached.

In the foregoing, the embodiment of the purifying method of HFO-1234yf of the present invention has been described with reference to one example of the embodiment of the purifying apparatus of the HFO-1234yf of the present invention for which a schematic diagram is illustrated in FIG. 1. In the purifying method of HFO-1234yf of the embodiment according to the present invention, moreover, it is preferred to add operations to subject the part of the distillate taken out from the unit for cooling and condensing to a dehydration treatment, and supply the obtained first treated product to the k-th stage (where "k" is an integer satisfying n+1≤k≤m) of the distillation column.

Figure 2:
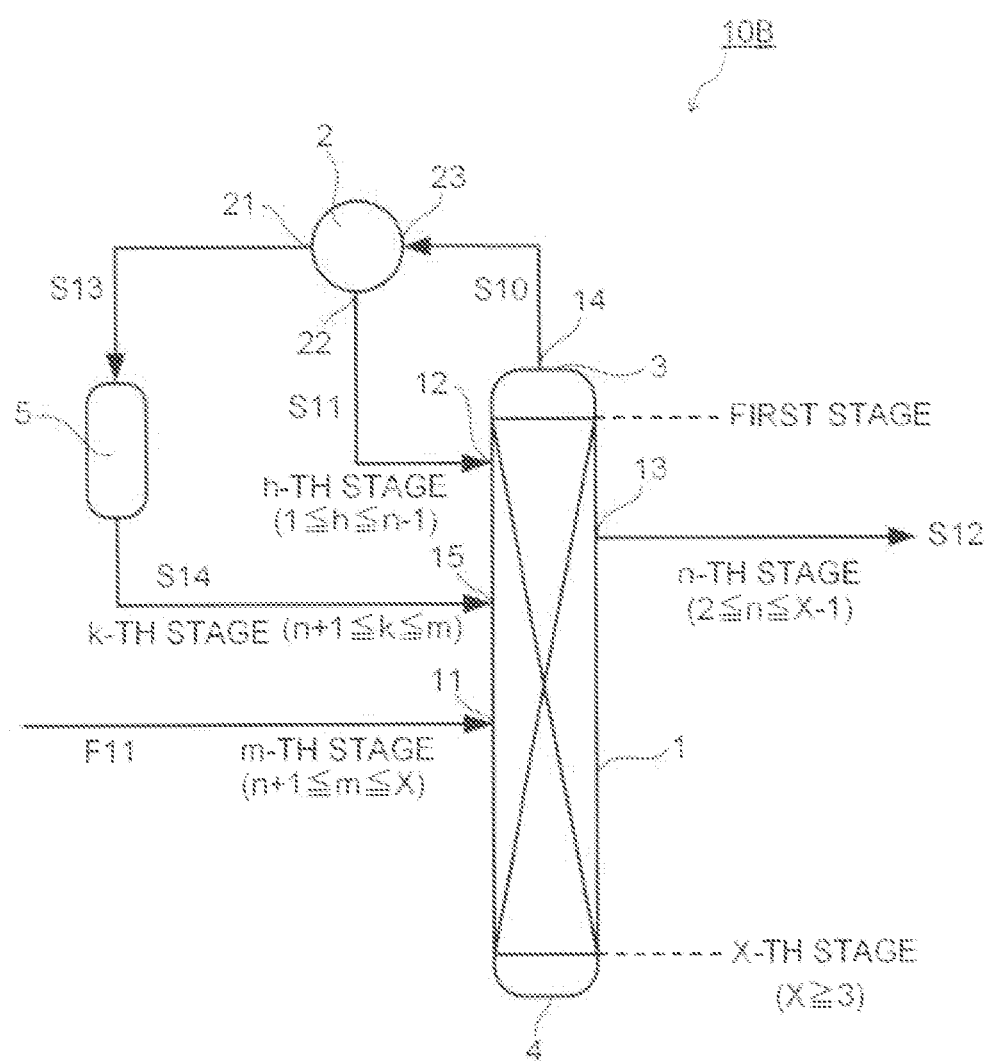
FIG. 2 is a schematic diagram illustrating a modification example of the embodiment of the purifying apparatus of HFO-1234yf of the present invention.

The embodiment of the purifying method of the present invention to which such operations are added can be carried out by using, for example, a modification example of an embodiment of the purifying apparatus of HFO-1234yf of the present invention whose schematic diagram is illustrated in FIG. 2.

A purifying apparatus 10B of this embodiment illustrated in FIG. 2 is similar to the purifying apparatus 10A except that a first dehydration treatment unit 5 which dehydrates the taken-out distillate S13 is further provided in the purifying apparatus 10A, and the distillation column 1 has, in the k-th stage (where "k" is an integer satisfying n+1≤k≤m), a first treated product supply port 15 for supplying a first treated product S14 which is dehydrated thereby to the distillation column 1.

As the first dehydration treatment unit 5 which dehydrates the taken-out distillate S13, specifically, there are following methods (a) to (d).

(a) Water is absorbed by a dehydrating agent through a dehydration column in which the dehydrating agent such as molecular sieve (synthetic zeolite), silica gel, or activated alumina is filled.

(b) Water is separated from organic components by a boiling point difference by using the distillation column.
(c) Water is absorbed by being brought into contact with concentrated sulfuric acid in a state of vapor phase by the dehydration column.
(d) Dehydrating agent such as magnesium sulfate is suspended in a state of liquid phase to let the dehydrating agent absorb water, and thereafter the dehydrating agent is removed by filtration or the like.

Among them, for the first dehydration treatment unit 5, using the dehydration column of (a) is preferred from the viewpoint of making operability and maintenance easy. When the dehydration column is used, if the limit of the amount of water that can be absorbed by the dehydrating agent filled in the dehydration column is exceeded, a breakthrough of water occurs and the amount of water contained in the first treated product at the exit of the dehydration column increases. Accordingly, at a point the water amount starts to increase, the dehydrating agent which absorbed water to its limit is replaced with a dehydrating agent capable of absorbing water. In order to allow replacing the dehydrating agent at a point the amount of water of the first treated product at the exit of the dehydration column starts to increase. In the apparatus according to the embodiment, it is preferred to have a device to monitor the amount of water in the first treated product at the exit of the dehydration column.

In the first dehydration treatment unit 5, the dehydration ability is set appropriately according to the amount of water contained in the taken-out distillate S13, the required water content for the first treated product S14 obtained by the dehydration treatment, and the required treated amount (rate) and the like. When the dehydration column is used, the type of the dehydrating agent, capacity, and so on are chosen appropriately in consideration of the frequency of replacing the dehydrating agent, and so on.

Note that as the water content in the first treated product S14 after the dehydration treatment, the mass ratio of water relative to HFO-1234yf in the first treated product S14 is preferably in the range of 100 ppm or less, more preferably 50 ppm or less, from the viewpoint of facilitating decrease of water in the product.

The k-th stage, which is the position where the first treated product supply port 15 for supplying the first treated product S14 to the distillation column 1 is provided, that is, the position where the first treated product S14 is supplied to the distillation column 1, is chosen appropriately from any stages of (n+1)-th stage to m-th stage. That is, the first treated product supply port 15 is provided in a stage that is lower than the purified product discharge port 13 disposed in the n-th stage through which the purified product S12 of HFO-134yf is taken out and is the same stage (m-th stage) as or higher stage than the supply port 11 of the crude HFO-1234yf (F11). Preferably, the first treated product supply port 15 in the embodiment according to the present invention is provided in the m-th stage and more preferably, the supply port 11 for supplying the crude HFO-1234yf is used as the first treated product supply port 15 as will be described below. The supply amount (mass/H) of the first treated product S14 to the distillation column 1 is preferably 0.03 to 0.1 times relative to the supply amount (mass/H) of F11. Further, the temperature of the first treated product S14 supplied to the distillation column 1 is preferably 20° C. to 80° C.

In the purifying method of HFO-1234yf of the embodiment according to the present invention, part of the distillate taken out from the unit for cooling and condensing may be subjected to the dehydration treatment, and the obtained first treated product may be supplied to the distillation column from the m-th stage of the distillation column together with the crude HFO-1234yf. Such an embodiment of the purifying method of the present invention can be carried out, for example, by using another modification example of the embodiment of the purifying apparatus of HFO-1234yf of the present invention whose schematic diagram is illustrated in FIG. 3.

Figure 3:
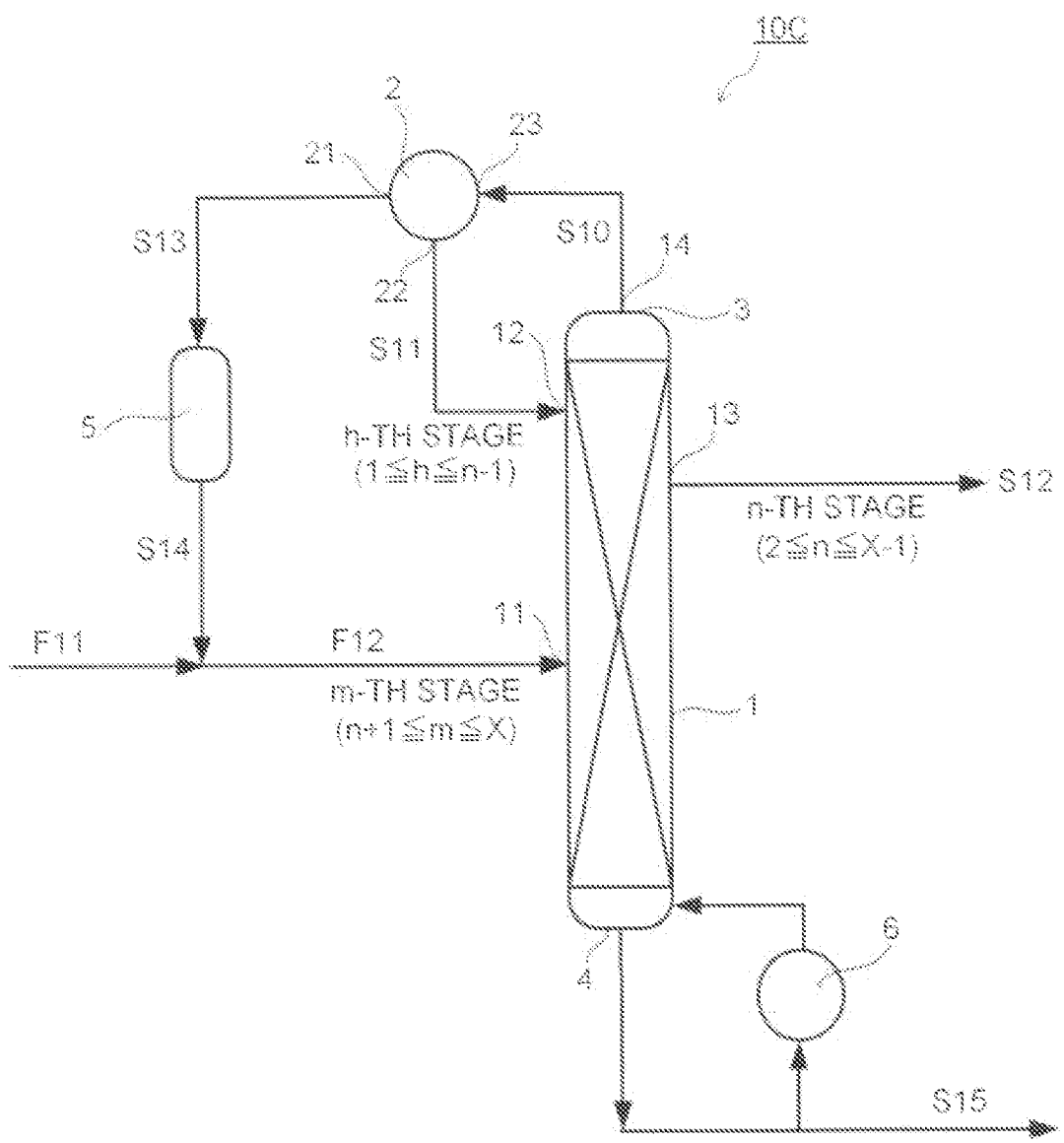
FIG. 3 is a schematic diagram illustrating another modification example of the embodiment of the purifying apparatus of HFO-1234yf of the present invention.

A purifying apparatus 10C of this embodiment illustrated in FIG. 3 is similar to the purifying apparatus 10B except having, instead of the device to supply the first treated product S14 to the k-th stage of the distillation column 1 in the purifying apparatus 10B, a device to merge this to a supply path of the crude HFO-1234yf, and having a device for taking out a bottom product from the column bottom 4 of the distillation column 1, taking out part S15 thereof, then heating the remainder in a heating unit 6, and returning the heated remainder to the vicinity of the column bottom 4 of the distillation column 1. Note that accompanying this, the distillation column 1 has a structure that does not have the first treated product supply port 15 in the k-th stage in the purifying apparatus 10C.

Further the device for taking out a bottom product from the column bottom 4 of the distillation column 1, taking out part S15 thereof, then heating the remainder in the heating unit 6, and returning the heated remainder to the vicinity of the column bottom 4 of the distillation column 1 is device which may be arbitrarily provided in the purifying apparatus of the embodiment according to the present invention. Heating the remainder of the bottom product and returning it to the vicinity of the column bottom 4 of the distillation column 1 in this manner can contribute to adjustment of temperature in the vicinity of the column bottom 4. The bottom product contains, with a higher concentration than those in the crude HFO-1234yf, organic impurities having a higher boiling point than HFO-1234yf contained in the crude HFO-1234yf. The part S15 taken out of the bottom product is used as a raw material or the like for manufacturing the aforementioned HFO-1234yf through another separating step and/or the like as necessary.

Here, in the purifying apparatus 10C, the supplied product F12 supplied to the distillation column 1 from the m-th stage of the distillation column 1 is a mixture of the crude HFO-1234yf (F11) supplied form the outside of the purifying apparatus 10C and the first treated product S14 generated inside the purifying apparatus 10C. The temperature and supply amount of such supplied product F12 can be similar to those in the case where the crude HFO-1234yf (F11) is supplied from the m-th stage to the distillation column 1 in the purifying apparatus 10A. That is, when purifying is performed using an apparatus similar to the purifying apparatus 10C, by setting Sw13:Fw12 in the case where the supply amount of the supplied product F12 (mass/H) is Fw12, similarly to the aforementioned value of Sw13:Fw11, the supplied product F12 in which content of water relative to HFO-1234yf is 100 ppm or less, preferably 50 ppm or less or the supplied product F12 in which content of water relative to HFO-1234yf is more than 20 ppm can be made as the HFO-1234yf purified product S12 in which content of water relative to HFO-1234yf is 20 ppm or less.

Further, when the purifying method of HFO-1234yf of the embodiment according to the present invention has the step of dehydrating the obtained taken-out distillate and supplying it to the distillation column, this step may also be performed by a method dehydrating the part of the distillate taken out from the unit for cooling and condensing together with the crude HFO-1234yf and supplying the obtained second treated product to the m-th stage of the distillation column. Such an embodiment of the purifying method of the present invention can be carried out by, for example, using still another modification example of the embodiment of the purifying apparatus of HFO-1234yf of the present invention whose schematic diagram is illustrated in FIG. 4.

Figure 4:
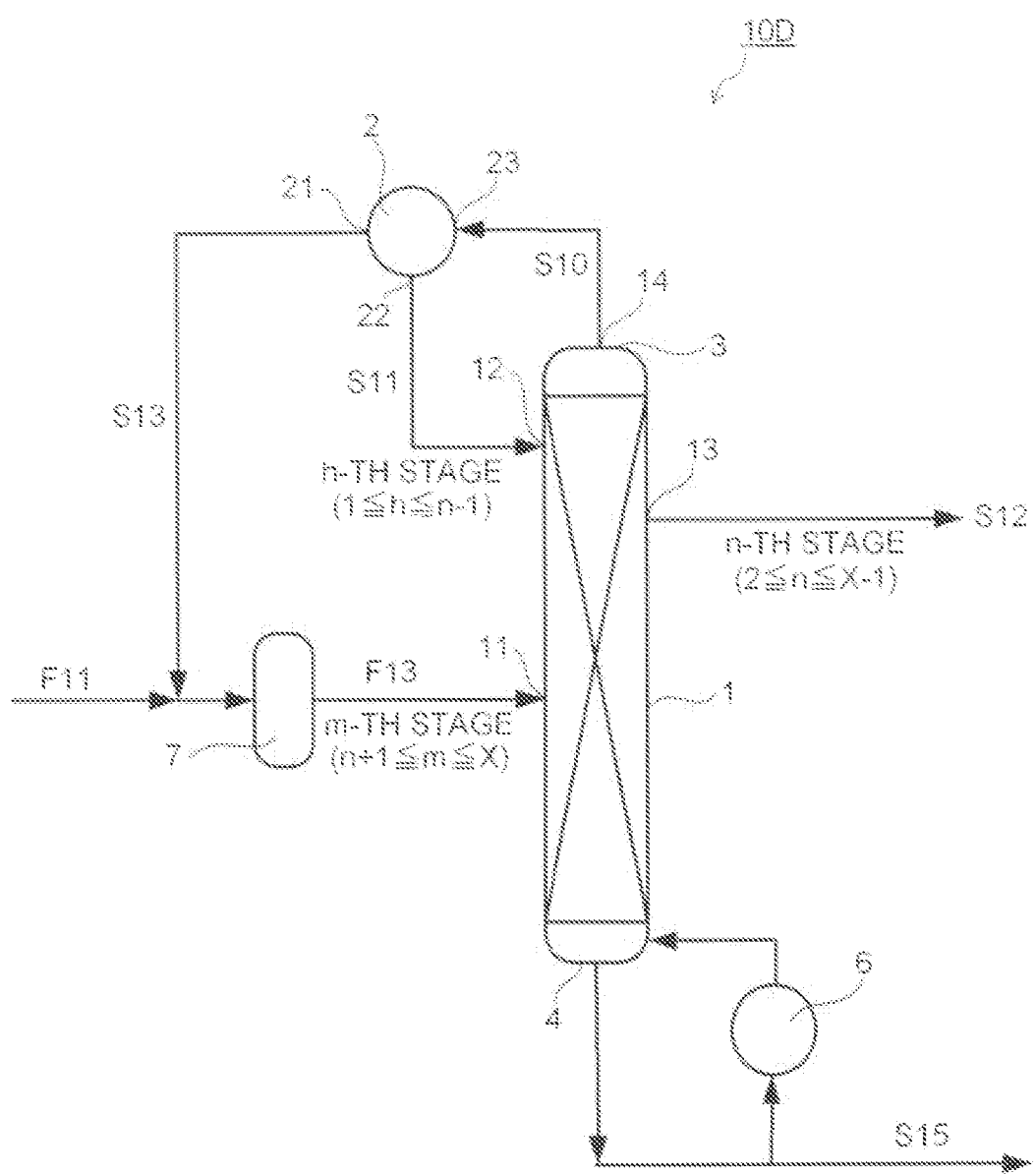
FIG. 4 is a schematic diagram illustrating still another modification example of the embodiment of the purifying apparatus of HFO-1234yf of the present invention.

A purifying apparatus 10D of this embodiment illustrated in FIG. 4 is similar to the purifying apparatus 10C except that the first dehydration treatment unit 5 for dehydrating the taken-out distillate S13 is not disposed in the purifying apparatus 10C, there is provided a device to merge the taken-out distillate S13 to the supply path of the crude HFO-1234yf and a second dehydration treatment unit 7 for dehydrating the taken-out distillate S13 after merged and the crude HFO-1234yf (F11) simultaneously, and a second treated product F13 dehydrated in this manner is supplied from the supply port 11 provided in the m-th stage of the distillation column 1 to the distillation column 1.

Further, the method for the second dehydration treatment unit 7 in the purifying apparatus 10D can be similar to ones for the first dehydration treatment unit 5 in the purifying apparatus 10B, 10C including the preferred modes. However, the treatment capability thereof is preferred to be a comparable treatment capability for dehydrating the total amount of the taken-out distillate S13 and the crude HFO-1234yf (F11). Moreover, although not illustrated, a first dehydration treatment unit 5 similar to the first dehydration treatment unit 5 provided in the purifying apparatus 10C illustrated in FIG. 3 may be provided as necessary in the purifying apparatus 10D.

Here, in the purifying apparatus 10D, the temperature and supply amount of the supplied product F13 supplied to the distillation column 1 from the m-th stage of the distillation column 1 can be similar to those in the case where the crude HFO-1234yf (F11) is supplied to the distillation column 1 from the m-th stage in the purifying apparatus 10A. That is, when purifying is performed using an apparatus similar to the purifying apparatus 10D by setting Sw13:Fw13 in the case where the supply amount of the supplied product F13 (mass/H) is Fw13 similarly to the aforementioned value of Sw13:Fw11, the supplied product F13 in which content of water relative to HFO-1234yf is 100 ppm or less, preferably 50 ppm or less or the supplied product F13 in which content of water relative to HFO-1234yf is more than 20 ppm can be made as the HFO-1234yf purified product S12 in which content of water relative to HFO-1234yf is 20 ppm or less.

Here, regarding the water content of the crude HFO-1234yf (F11), when the purifying method of the embodiment according to the present invention includes the dehydration treatment of the crude HFO-1234yf (F11) as the target of treatment by using the purifying apparatus 10D, or the like, the content of water relative to HFO-1234yf in the crude HFO-1234yf (F11) may be, for example, about 0.1 mass % to 0.3 mass %. However, when the purifying method of the embodiment according to the present invention does not include the dehydration treatment of the crude HFO-1234yf (F11), in order to obtain the HFO-1234yf purified product in which content of water relative to HFO-1234yf is 20 ppm or less, preferably, the crude HFO-1234yf obtained form the reaction system is dehydrated in advance by a method similar to the aforementioned dehydration treatment so that the content of water relative to HFO-1234yf is 100 ppm or less as the crude HFO-1234yf (F11).

Manufacturing Method

The manufacturing method of HFO-1234yf of the embodiment according to the present invention is a manufacturing method including the above-described purifying method. The manufacturing method of HFO-1234yf of the embodiment according to the present invention is, specifically, a manufacturing method having the following step (A) and step (B).

(A) Step of causing a reaction of raw material chemical compounds to obtain crude HFO-1234yf containing water and organic impurities.

(B) Step of purifying the crude HFO-1234yf obtained in the step (A) by the purifying method of the embodiment according to the present invention.

In the reaction step (A), although the method for obtaining the crude HFO-1234yf is not particularly limited, examples of the method include 1) obtaining it via the reaction route (1) by using an isomer mixture of HCFC-225 as a raw material, 2) obtaining it via the reaction route (2) by using PFO-1216yc as a raw material chemical compound, 3) obtaining it via the reaction route (3) by using 1,2,3-trichloropropane as a raw material chemical compound, and 4) obtaining by using 1,1,2,3-tetrachloropropene as a raw material chemical compound, and the like.

By these methods, the obtained crude HFO-1234yf contains water used in the reaction process together with organic impurities of non-reacted raw material chemical compounds, intermediates, by-products, and the like.

In the purifying step (B), by purifying the crude HFO-1234yf containing water and organic impurities obtained in the reaction step (A) by the purifying method of the embodiment according to the present invention, highly pure HFO-1234yf whose contents of organic impurities and water are both small can be obtained.

Here, in order to obtain HFO-1234yf with higher purity, in the reaction step (A), it is preferred to control reaction conditions by a conventional known method so that the content of the organic impurities whose boiling point are particularly close to that of HFO-1234yf or is specifically in the range of −40° C. to −10° C. does not become 10 mass % or more relative to the amount of HFO-1234yf in the obtained crude HFO-1234yf.

Further, when the content of water in the crude HFO-1234yf is of an amount more than 100 ppm relative to the amount of HFO-1234yf, it can be difficult to have the water content of 20 ppm or less relative to HFO-1234yf which is desired in the HFO-1234yf purified product obtained in the purifying step (B), and thus it is preferred to further provide a step of dehydration treatment before the purifying step (B).

In the manufacturing method of the embodiment according to the present invention, the HFO-1234yf purified product can thus be manufactured in which the content of HFO-1234yf relative to the total amount of the organic compounds content in the obtained purified product is 99.5 mass % or more, furthermore preferably 99.8 mass % or more, and the water content is quite low, preferably, the water content relative to HFO-1234yf is 20 ppm or less.

In the foregoing, the purifying method and the purifying apparatus of HFO-1234yf and the manufacturing method of HFO-1234yf of the embodiment according to the present invention has been described with examples, but their structures can be changed appropriately within a limit not departing from the spirit of the present invention or as necessary.

EXAMPLES

Hereinafter, the embodiment according to the present invention will be described specifically by way of examples, but the invention is not limited to these examples.

Example 1

The crude HFO-1234yf obtained in the method of the above reaction route (1) was purified by using the following purifying apparatus.

Purifying Apparatus

A purifying apparatus, similar to the purifying apparatus 10D illustrated in FIG. 4, including the distillation column 1, the unit 2 for cooling and condensing, the second dehydration unit 7 and the heating unit 6 was used.

As the distillation column 1, a distillation column 1 with an inside diameter of 550 mm, being made of SUS316L and having the total number X of stages of 25 was used. The distillation column 1 was structured to have the supply port 11 in the 21st stage (corresponding to the aforementioned "m-th stage") supplying the supplied product F13 resulted from subjecting the crude HFO-1234yf (F11) and the taken-out distillate S13 obtained from the unit 2 for cooling and condensing together to the dehydration treatment in the second dehydration unit 7, the purified product discharge port 13 in the second stage (corresponding to the aforementioned "n-th stage") through which the HFO-1234yf purified product S12 is taken out, and the recirculation liquid supply port 12 supplying the recirculation liquid (recirculation distillate) S11 sent from the unit 2 for cooling and condensing in the first stage (corresponding to the aforementioned "h-th stage").

The unit 2 for cooling and condensing has the distillate supply port 23 receiving supply of the distillate S10 taken out from the column top 3 of the distillation column 1, the distillate discharge port 21 taking out the part (taken-out distillate) S13 of the distillate as a vapor phase or a cooled and condensed liquid phase, and the recirculation liquid discharge port 22 taking out the remainder (recirculation distillate) S11 as the recirculation liquid recirculated to the distillation column 1 after it is cooled and condensed. As the second dehydration unit 7, a dehydration column having a column of 6 m³ filled with the molecular sieve as the dehydrating agent was used. Further, it was designed to take out the bottom product from the column bottom 4 of the distillation column 1 and take out the part S15 thereof, and return the remainder to the vicinity of the column bottom 4 of the distillation column 1 after it is heated by the heating unit 6.

Purifying the Crude HFO-1234yf

A treated product obtained by passing the crude HFO-1234yf (F11) through the dehydration column 7 was supplied as the supplied product F13 to the 21st stage of the distillation column 1 by supply amount of 605 kg/H, thereby starting the operation of the purifying apparatus. The distillation column 1 was set such that the pressure setting is 0.7 MPa, the temperature in the vicinity of the column top 3 is approximately 30° C., and the temperature in the vicinity of the column bottom 4 is approximately 120° C. From the start of operation of the purifying apparatus, an initial operation was performed for 1 to 24 hours until the material balance and composition reach an equilibrium state between supplied products (such as supplied product S13, recirculation liquid (recirculation product) S11, and liquid phase supplied form the heating unit to the column bottom) and discharged products (such as HFO-1234yf purified product S12 and bottom product) in the distillation column 1 coupled to the unit 2 for cooling and condensing, the dehydration column 7, and the heating unit 6. Thereafter, the crude HFO-1234yf was purified through a continuous operation in the obtained equilibrium state. Supply amount, discharge amounts, and compositions of substances in the purifying apparatus during the time in this equilibrium state were as presented below.

The distillate S10 taken out by 300 kg/H from the column top 3 of the distillation column 1 was supplied to the unit 2 for cooling and condensing, part thereof was taken out by amount of 32 kg/H as the taken-out distillate S13 in a vapor or liquid phase state, thereafter the total amount thereof was merged to the supply path of the crude HFO-1234yf (F11) and passed through the dehydration column 7, and then an obtained treated product was supplied continuously to the 21st stage of the distillation column 1 by supply amount of 605 kg/H as the supplied product F13.

The remainder (recirculation distillate) S11 resulted from removing the taken-out distillate S13 from the distillate S10 supplied from the column top 3 of the distillation column 1 to the unit 2 for cooling and condensing was changed to a liquid phase by cooling and condensing, and thereafter recirculated to the first stage of the distillation column 1 by supply amount of 268 kg/H as recirculation liquid having a liquid temperature of approximately 30° C.

On the other hand, a liquid phase part was taken out by discharge amount of 50 kg/H as the HFO-1234yf purified product S12 from the second stage of the distillation column 1. The bottom product was taken out by discharge amount of 723 kg/H from the column bottom 4 of the distillation column 1, and part thereof was heated to approximately 100° C. with the heating unit 6 and returned to the vicinity of the column bottom 4 by amount of 200 kg/H. The amount of the remainder S15 of the bottom product was 523 kg/H.

Table 1 presents compositions of the supplied product F13 as the treated product obtained by merging the taken-out distillate S13 to the supply path of the crude HFO-1234yf (F11) and passing it through the dehydration column 7, the remainder (recirculation distillate) S11, the HFO-1234yf purified product S12, and the remainder S15 of the bottom product in the purifying apparatus during the time in this equilibrium state. Note that the composition of the crude HFO-1234yf (F11) can be calculated form the above flow amounts (605 kg/H and 32 kg/H) of F13 and S13, and the compositions of F13 and S13 present in Table 1 below and the dehydration capability of the dehydration column 7.

As can be seen from Table 1, in the obtained HFO-1234yf purified product S12, the content of HFO-1234yf relative to the total amount of the organic compounds was 99.95 mass % and the content of water relative to HFO-1234yf was 9.0 ppm.

TABLE 1

| Fraction | | F13 | S11 | S12 | S15 |
|---|---|---|---|---|---|
| Content (wt %) relative to the total amount of the organic compounds | HFO-1234yf | 13.68 | 99.99 | 99.95 | 0.48 |
| | HFO-1243zf | 1.86 ppm | 9.26 ppm | 10.95 ppm | 0.57 ppm |
| | HFC-254eb | 9.37 | 0.01 | 0.04 | 10.80 |
| | HCFO-1224yd | 11.13 | 0.00 | 0.00 | 12.84 |
| | CFO-1214ya | 54.86 | 0.00 | 0.00 | 63.26 |
| | HCFC-225ca | 7.88 | 0.00 | 0.00 | 9.09 |
| | HCFC-225cb | 2.58 | 0.00 | 0.00 | 2.97 |
| | Other | 0.50 | 0.00 | 0.00 | 0.56 |

TABLE 1-continued

| Fraction | F13 | S11 | S12 | S15 |
|---|---|---|---|---|
| Water amount (relative to the total amount of the organic compounds) | 6.2 ppm | 33.4 ppm | 9.0 ppm | 0.9 ppm |
| Water amount (relative to the mass of HFO-1234yf) | 45.3 ppm | 33.4 ppm | 9.0 ppm | 187.5 ppm |

Example 2

Distillation was carried out similarly to example 1 except that the content of water contained in the crude HFO-1234yf (F11) is higher than that of example 1, specifically, distillation was carried out similarly to example 1 except that the water contained in the supplied product F13 in the purifying apparatus during the time in the equilibrium state is 13 ppm relative to the total amount of the organic compounds and the content of water relative to HFO-1234yf is 112 ppm. As a result, in the HFO-1234yf purified product S12-1 obtained from the purified product discharge port 13 of the distillation column 1, the content of HFO-1234yf relative to the total amount of the organic compounds was 99.9 mass % or more, the water amount relative to the total amount of the organic compounds was 40 ppm, and the content of water relative to HFO-1234yf was 40 ppm.

Example 3

Figure 5:
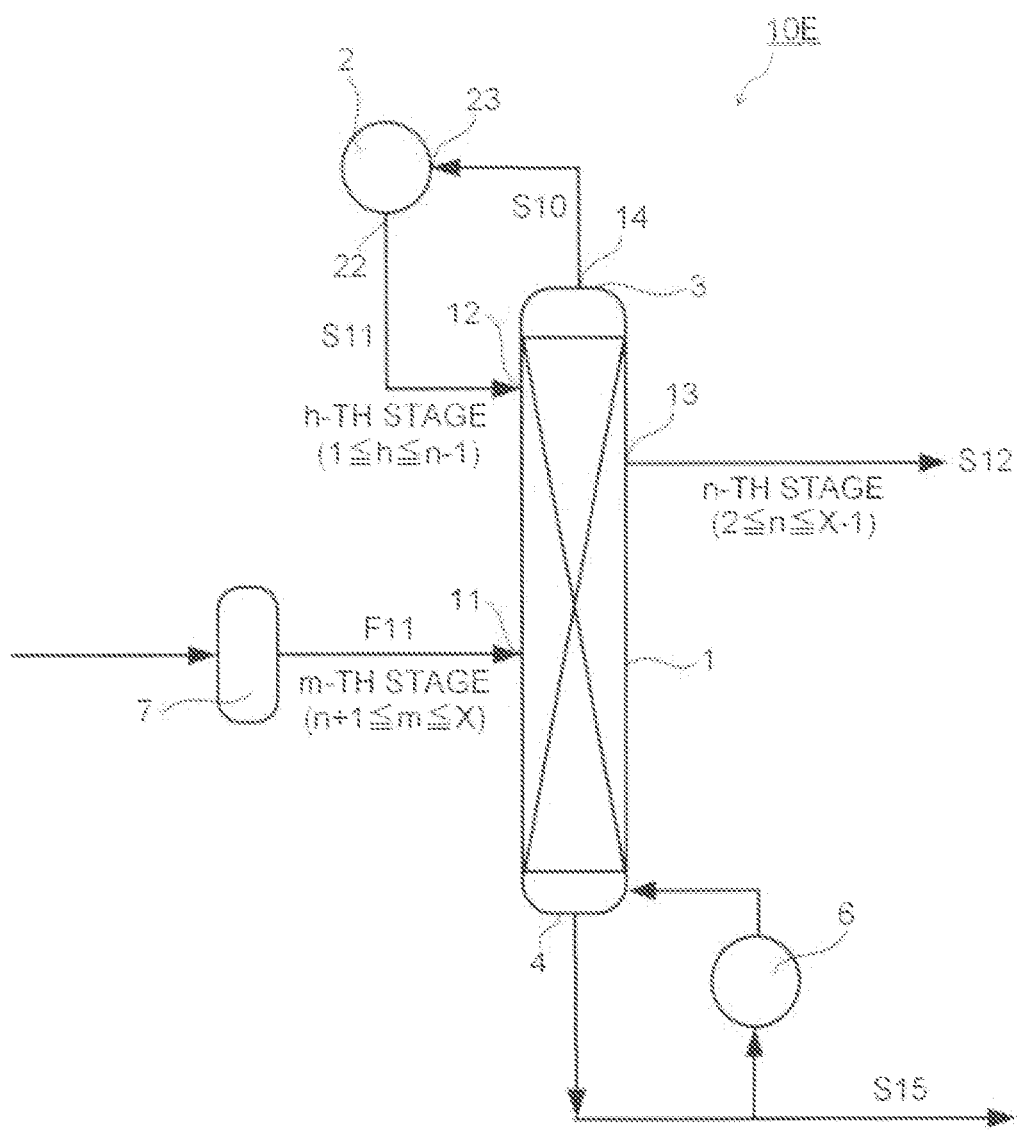
FIG. 5 is a diagram illustrating a purifying apparatus of HFO-1234yf used in example 3.

The crude HFO-1234yf (F11) used in example 1 was purified using a purifying apparatus 10E illustrated in FIG. 5. The purifying apparatus 10E is similar to that of example 1 except that the unit 2 for cooling and condensing does not have the distillate discharge port 21 through which the part (taken-out distillate) S13 of the distillate is taken out from the purifying apparatus used in example 1.
Here, in the crude HFO-1234yf (F11) supplied to the distillation column 1 via the dehydration column 7, the content of HFO-1234yf relative to the total amount of the organic compounds was 13.0 mass %, the water amount relative to the total amount of the organic compounds was 6.5 ppm, and the content of water relative to HFO-1234yf was 50.0 ppm. Then, in the HFO-1234yf purified product S12 obtained from the purified product discharge port 13 of the distillation column 1, the content of HFO-1234yf relative to the total amount of the organic compounds was 99.9 mass % or more, the water amount relative to the total amount of the organic compounds was 46 ppm, and the content of water relative to HFO-1234yf was 46 ppm. The water amount of the HFO-1234yf purified product S12 was a high value compared to example 1 but it is a low value compared to the content of water relative to HFO-1234yf in the recirculation liquid (recirculation distillate) S11.

Comparative Example 1

Figure 6:
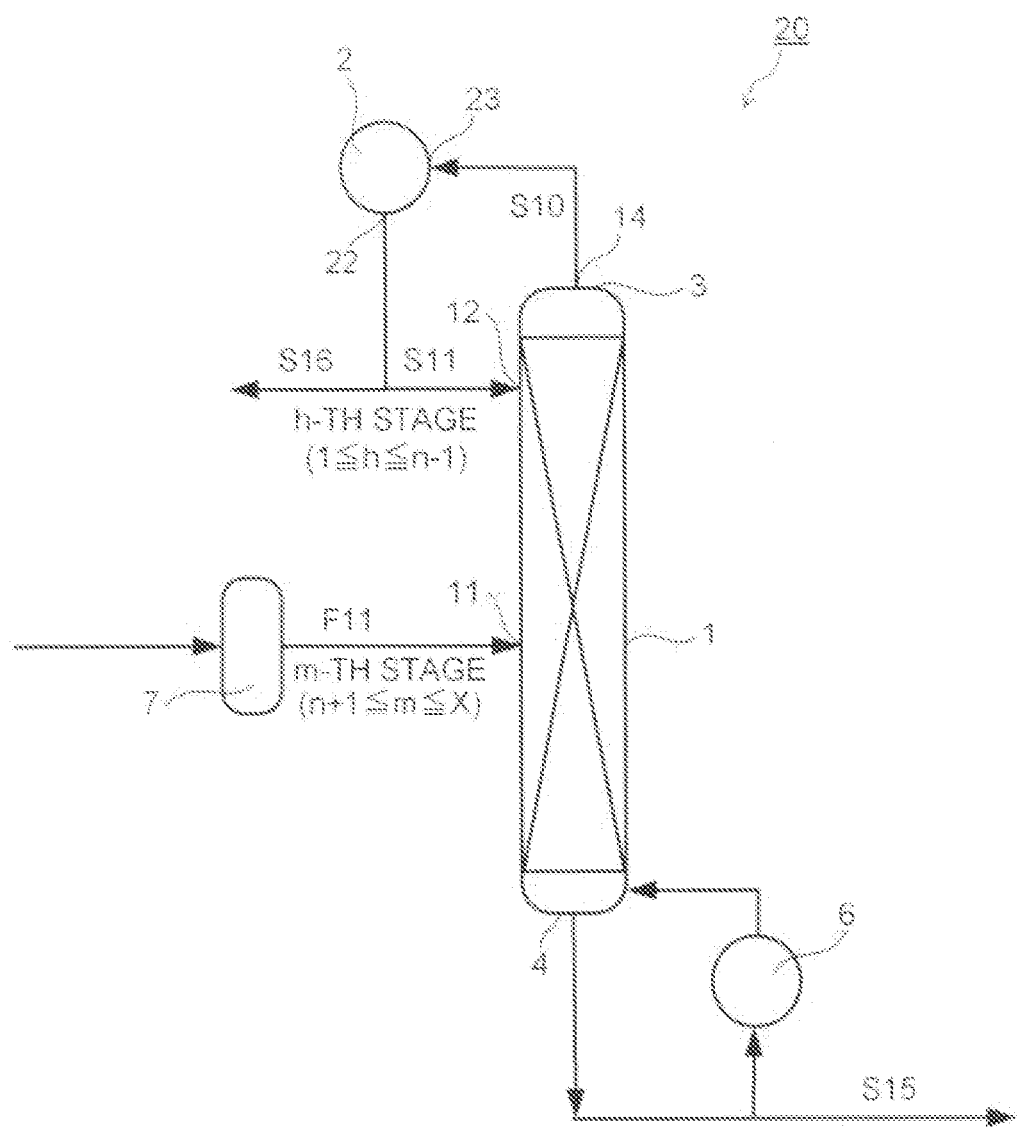
FIG. 6 is a diagram illustrating a purifying apparatus of HFO-1234yf used in comparative example 1.

The crude HFO-1234-yf (F11) used in example 1 was purified using a purifying apparatus 20 illustrated in FIG. 6. The purifying apparatus 20 is similar to that of example 1 except that, in the purifying apparatus used in example 1, the distillation column 1 does not have the purified product discharge port 13 in the second stage through which the HFO-1234yf purified product S12 is taken out and moreover the unit 2 for cooling and condensing does not have the distillate discharge port 21 through which the part (taken-out distillate) S13 of the distillate is taken out, and instead, the part of the recirculation liquid S11 obtained from the distillate S10 by the unit 2 for cooling and condensing is recirculated to the distillation column 1 and the remainder is taken out as a HFO-1234yf purified product S16.
As a result, the content of HFO-1234yf relative to the total amount of the organic compounds in the obtained HFO-1234yf purified product S16 was 99.9 mass % or more, the water amount relative to the total amount of the organic compounds was 220 ppm, and the content of water relative to HFO-1234yf was 220 ppm.

Comparative Example 2

Figure 7:
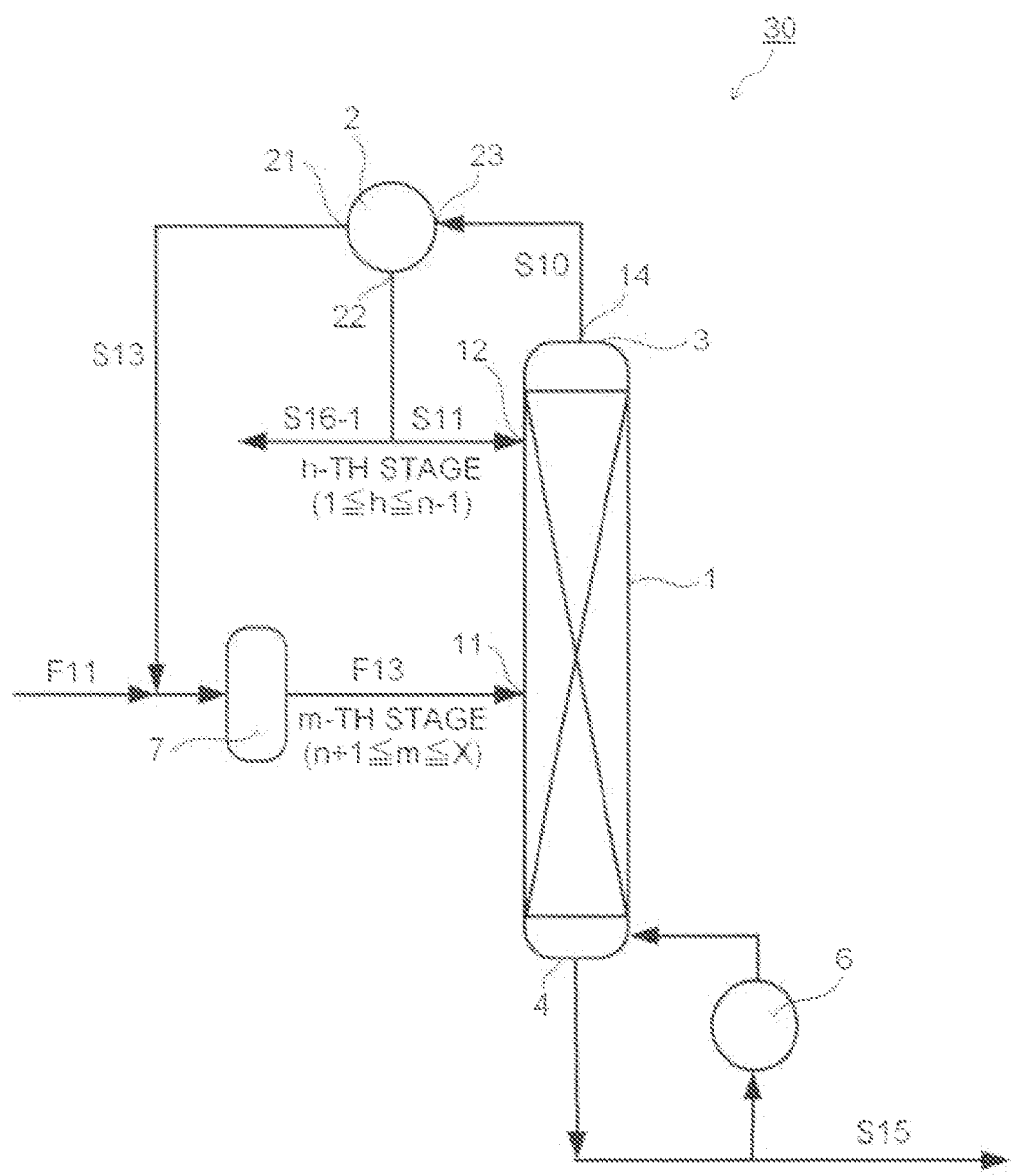
FIG. 7 is a diagram illustrating a purifying apparatus of HFO-1234yf used in comparative example 2.

The crude HFO-1234yf (F11) used in example 1 was purified using a purifying apparatus 30 illustrate in FIG. 7. The purifying apparatus 30 is similar to that of example 1 except that, in the purifying apparatus used in example 1, the distillation column 1 does not have the purified product discharge port 13 in the second stage through which the HFO-1234yf purified product S12 is taken out, and instead the part of the recirculation liquid S11 obtained from the remainder of the distillate S10 by the unit 2 for cooling and condensing is recirculated to the distillation column 1 and the remainder is taken out as a HFO-1234yf purified product S16-1.
As a result, the content of HFO-1234yf relative to the total amount of the organic compounds in the obtained HFO-1234yf purified product S16-1 was 99.9 mass % or more, the water amount relative to the total amount of the organic compounds was 233 ppm, and the content of water relative to HFO-1234yf was 223 ppm. As compared to the HFO-1234yf purified product S16 of comparative example 1, the water amount contained in the HFO-1234yf purified product S16-1 was about the same, and the water amount was still a high value compared to example 1.

According to the present invention, 2,3,3,3-tetrafluoropropene with quite low GWP of 4, which is useful as an alternative refrigerant for HFO-134a, can be purified efficiently as a highly pure purified product with low contents of both organic impurities and water.

What is claimed is:
1. A method for continuously purifying crude 2,3,3,3-tetrafluoropropene containing water and an organic impurity, the method comprising:
   using an apparatus having a distillation column with X stages (where "X" is an integer of 3 or larger, and the stage closest to a column top is the first stage) and a unit for cooling and condensing a distillate taken out from a column top of the distillation column;
   supplying the crude 2,3,3,3-tetrafluoropropene to an m-th stage (where "m" is an integer satisfying n+1≤m≤X and "n" is an integer satisfying 2≤n≤X−1) of the distillation column;
   recirculating at least part of the distillate cooled and condensed in the unit for cooling and condensing to an h-th stage (where "h" is an integer satisfying 1≤h≤n−1) of the distillation column; and
   taking out a liquid phase part of an n-th stage of the distillation column to obtain a purified product of 2,3,3,3-tetrafluoropropene.

2. The purifying method of 2,3,3,3-tetrafluoropropene according to claim 1,
   wherein the organic impurity includes an organic compound having boiling point of from −40° C. to −10° C.

3. The purifying method of 2,3,3,3-tetrafluoropropene according to claim 1, wherein the organic impurity includes at least one selected from the group consisting of 3,3,3-trifluoropropene, 3,3-difluoropropene, 1,2,3,3,3-pentafluoropropene, 1,3,3,3-tetrafluoropropene, 1,1,3,3,3-pentafluoropropene, 1,1,2,3,3,3-hexafluoropropene, and 1,1,1,2,2-pentafluoropropane.

4. The purifying method of 2,3,3,3-tetrafluoropropene according to claim 1,
wherein a content of 2,3,3,3-tetrafluoropropene to a total amount of organic compounds in the crude 2,3,3,3-tetrafluoropropene is 5 mass % or more and less than 99.5 mass %, and a content of 2,3,3,3-tetrafluoropropene to a total amount of organic compounds in the purified product of 2,3,3,3-tetrafluoropropene is 99.5 mass % or more.

5. The purifying method of 2,3,3,3-tetrafluoropropene according to claim 1,
wherein a content of water to 2,3,3,3-tetrafluoropropene in the crude 2,3,3,3-tetrafluoropropene is 100 ppm or les, and a content of water to 2,3,3,3-tetrafluoropropene in the purified product of 2,3,3,3-tetrafluoropropene is 20 ppm or less.

6. The purifying method of 2,3,3,3-tetrafluoropropene according to claim 1,
wherein part of the distillate is taken out from the unit for cooling and condensing, and a remainder is recirculated as recirculation liquid to the h-th stage (where "h" is an integer satisfying $1 \leq h \leq n-1$) of the distillation column.

7. The purifying method of 2,3,3,3-tetrafluoropropene according to claim 6,
wherein the part of the distillate taken out from the unit for cooling and condensing is subjected to a dehydration treatment, and an obtained first treated product is supplied to a k-th stage (where "k" is an integer satisfying $n+1 \leq k \leq m$) of the distillation column.

8. The purifying method of 2,3,3,3-tetrafluoropropene according to claim 7,
wherein a content of water to 2,3,3,3-tetrafluoropropene in the first treated product is 100 ppm or less.

9. The purifying method of 2,3,3,3-tetrafluoropropene according to claim 7,
wherein the first treated product is supplied together with the crude 2,3,3,3-tetrafluoropropene to the m-th stage of the distillation column.

10. The purifying method of 2,3,3,3-tetrafluoropropene according to claim 6,
wherein distillate of part taken out from the unit for cooling and condensing is subjected to a dehydration treatment together with the crude 2,3,3,3-tetrafluoropropene, and an obtained second treated product is supplied to the m-th stage of the distillation column.

11. The purifying method of 2,3,3,3-tetrafluoropropene according to claim 7,
wherein the dehydration treatment is performed by passing through a dehydration column.

12. A manufacturing method of 2,3,3,3-tetrafluoropropene,
the method comprising the purifying method according to claim 1.

* * * * *